United States Patent [19]

Phillips et al.

[11] Patent Number: 4,870,157
[45] Date of Patent: Sep. 26, 1989

[54] SELECTED 4-ACYL-2,6-DIALKYLPHENOL ADDUCTS OF SACCHARIDES AND THEIR USE AS STABILIZERS OF ORGANIC MATERIALS AGAINST OXIDATIVE DEGRADATION

[75] Inventors: Steven D. Phillips, Northford; Bonnie B. Sandel, Milford, both of Conn.

[73] Assignee: Olin Corporation, Cheshire, Conn.

[21] Appl. No.: 753,093

[22] Filed: Jul. 9, 1985

[51] Int. Cl.$^4$ .................. C08K 50/07; C07H 15/00
[52] U.S. Cl. ........................... 524/58; 536/1.1;
    536/4.1; 536/18.5; 536/124; 524/583; 524/585
[58] Field of Search .................... 536/1.1, 4.1; 514/23,
    514/25; 524/58

[56] References Cited

U.S. PATENT DOCUMENTS

| | | | |
|---|---|---|---|
| 3,285,855 | 11/1966 | Dexter et al. | 252/57 |
| 3,862,121 | 1/1975 | Jaques et al. | 260/210 R |
| 3,931,103 | 1/1976 | Hardy | 260/45.85 B |
| 3,975,360 | 8/1976 | Kline | 260/45.85 R |
| 4,364,930 | 12/1982 | Griat et al. | 424/81 |
| 4,465,673 | 8/1984 | Tanaka et al. | 424/180 |

*Primary Examiner*—Johnnie R. Brown
*Assistant Examiner*—Elli Peselev
*Attorney, Agent, or Firm*—William A. Simons

[57] ABSTRACT

Disclosed are selected 4-acyl-2,6-dialkylphenyl adducts of mono- and polysaccharides, which are useful an antioxidants in organic materials (e.g. polyolefins) normally subject to oxidative degradation.

29 Claims, No Drawings

SELECTED 4-ACYL-2,6-DIALKYLPHENOL ADDUCTS OF SACCHARIDES AND THEIR USE AS STABILIZERS OF ORGANIC MATERIALS AGAINST OXIDATIVE DEGRADATION

BACKGROUND OF THE INVENTION

1. Field of the Invention

The present invention is directed to selected 4-acyl-2,6-dialkylphenol adducts of saccharides and their use as stabilizers of organic materials against oxidative degradation.

2. Description of the Prior Art

Many organic materials suffer oxidative degradation. This problem is particularly acute in plastics and other synthetic polymers where degradation may readily occur under the high temperatures normally associated with their processing. Degradation also results in such polymers after long-term aging under ambient conditions. In order to stabilize or protect these organic materials from oxidative degradation, certain antioxidant chemical additives have been incorporated into these materials either before or during processing.

It is also known to use combinations of antioxidant additives to improve oxidative stability. Certain combinations of antioxidants provide a synergistic amount of antioxidant activity. See U.S. Pat. No. 3,535,277, which issued to Miller et al on Oct. 20, 1970. Such combinations may be made by reacting together two or more antioxidant additives to form a single compound having two or more antioxidant moieties. This approach is taught in U.S. Pat. Nos. 4,413,077, which issued to Valdiserri et al on Nov. 1, 1983, and 4,414,408, which issued to Cottman on Nov. 8, 1983.

2,6-Dialkyl substituted phenols are well known in the art as antioxidant moieties. Furthermore, the reaction of such moieties with other antioxidant moieties to provide multifunctional antioxidant molecules is known. See U.S. Pat. Nos. 3,285,855, which issued to Dexter et al on Nov. 15, 1966; 3,526,668, which issued to Starnes et al on Sept. 1, 1970; and 3,975,360, which issued to Kline on Aug. 17, 1976.

These 2,6-dialkyl substituted or hindered phenolic stabilizers, while being reasonably effective stabilizers for organic materials, may have operating problems associated with them. Specifically, they are known to cause discoloration or staining to some organic materials they intend to stabilize. They also may be too readily volatilized, and, therefore, will escape from the material they are stabilizing. This will result in a lowered antioxidant level and will shorten the service life of that material.

In view of these facts, there is a need for new antioxidants or stabilizers which have improved effectiveness against oxidative degradation over a wide variety of applications.

It is therefore an object of this invention to provide a new class of relatively nondiscoloring and nonvolative hindered phenolic stabilizers for oxidizable organic materials.

These and other objects of the invention will be apparent from the following detailed description of the invention.

BRIEF SUMMARY OF THE INVENTION

The foregoing objects are accomplished by the present invention which is directed to organic materials, including polyolefins, containing an effective stabilizing amount against oxidative degradation of a 4-acyl-2,6-dialkylphenol adduct of a saccharide derived from either formula (I) or (II):

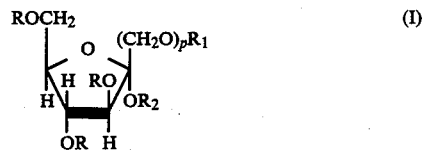

(I)

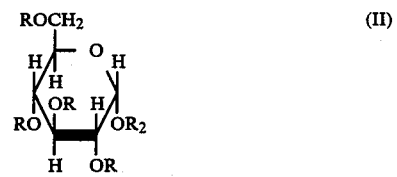

(II)

wherein p is defined as being 0 or 1; R is defined as a hydrogen or 4-acyl-2,6-dialkylphenol of formula (III):

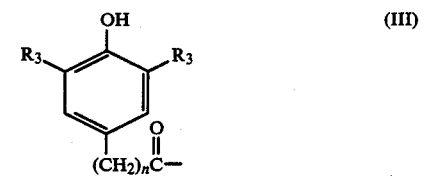

(III)

with the proviso that at least one of said R in formulae (I) or (II) is said 4-acyl-2,6-dialkylphenol; $R_1$ is selected as a hydrogen when $p=0$ and as a R when $p=1$; $R_2$ is selected from the group consisting of hydrogen and a lower alkyl group having 1 to 4 carbon atoms; and $R_3$ is selected from the group consisting of branched alkyl groups having about 4 to about 8 carbon atoms; and n is defined as being from 0 to 10.

The present invention is also directed to the process of using these 4-acyl-2,6-dialkylphenol adducts as antioxidants or oxidative stabilizers in organic materials that are normally subject to oxidative degradation. These organic compounds include polyolefins, such as polyethylene and polypropylene.

Another embodiment of the present invention is directed to these 4-acyl-2,6-dialkylphenol adducts of saccharides, as defined above, as novel compositions of matter.

DETAILED DESCRIPTION

The hindered phenolic-substituted saccharides of formulae (I) and (II) may be prepared by reacting the corresponding hindered phenolic-substituted carboxylic acid halide with the desired saccharide, preferably in the presence of an inert solvent. This reaction is illustrated by reacting 4 moles of 2-(3,5-di-tert-butyl-4-hydroxyphenyl)propanoyl chloride with methyl glucoside to form the desired tetra-adduct, as shown in the following equation (A):

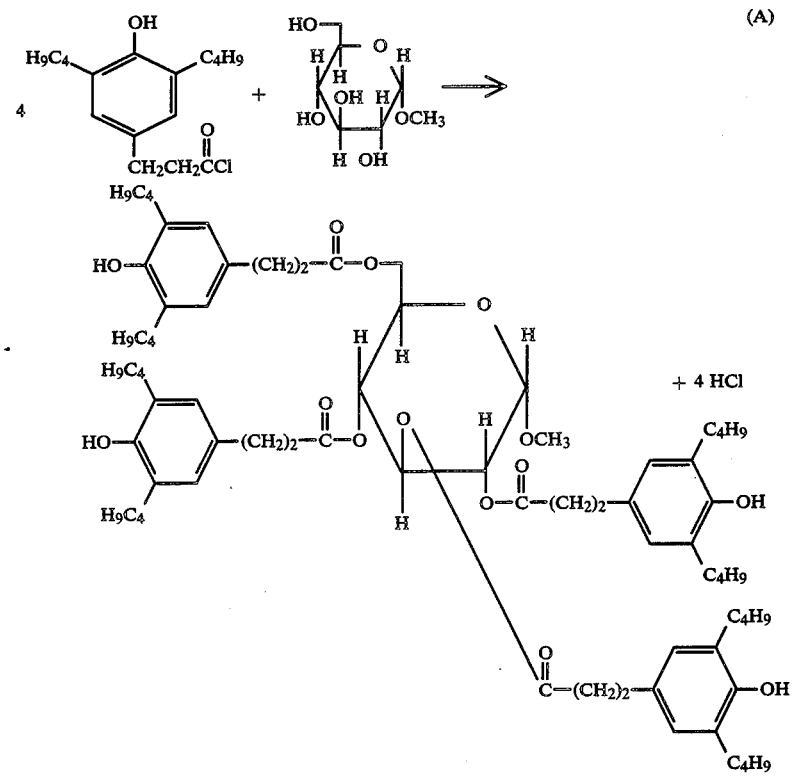

(A)

The hindered phenolic carboxylic acid halides which may be used as starting reactants for the adducts of the present invention include those of the following formula (IV):

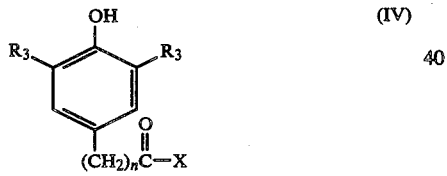

(IV)

wherein each $R_3$ and n are as defined above. Preferred branched alkyl substitutents include isobutyl, t-butyl, isohexyl and the like. The most preferred $R_3$ group is t-butyl. The preferred range for n is from about 2 to about 6. X is a halogen atom (e.g. Cl, Br and I). Cl is preferred because of cost.

In addition to the methyl glucosides shown in equation (A), above, the term "saccharide" as used in the present specification and claims includes monosaccharides of formulae (I) and (II), above, and polysaccharides (e.g. disaccharides) derived from these monosaccharide structures. The saccharide structures of formulae (I) and (II) include all stereoisomers of the glucose, fructose or xylose shown. These include members of the sugar families of aldoses having five or six carbon atoms; 2-ketoses having six carbon atoms; and disaccharides derived from or based upon these monosaccharides. Suitable examples are listed below:

Aldoses Having Six Carbon Atoms

D-Allose
D-Altrose
D-Glucose
D-Mannose
D-Gulose
D-Idose
D-Galactose
D-Talose

Aldoses Having Five Carbon Atoms

D-Ribose
D-Arabinose
D-Xylose
D-Lyxose

2-Ketoses Having Six Carbon Atoms

D-Psicose
D-Fructose
D-Sorbose
D-Tagatose

Disaccharides

Sucrose

Lower alkyl substituted-saccharides ($R_2$=a lower alkyl group having 1 to 4 carbon atoms) of these sugars may also be employed. Methyl glucoside adducts are particularly preferred.

The molar ratio between the above-noted hindered phenolic carboxylic acid halide and the saccharide will depend upon the number of hindered phenolic groups desired on the saccharide. Thus, at least one mole and up to four moles of the hindered phenol may be added on each monosaccharide molecule. Generally, it is believed to be desirable to use a molar excess (e.g. up to about 25%) of the hindered phenol over the saccharide to ensure adequate reaction yield and rate.

The reaction to make these adducts of formulae (I) and (II) is preferably run in the presence of a base which serves to catalyze the reaction and remove HCl from the reaction mixture as a hydrochloride salt. Common bases which may be used include triethylamine, N,N-dimethylaniline, pyridine, 4-(dimethylamino)-pyridine and the like. In certain cases, as with pyridine, the base may also serve as a suitable solvent for the reaction mixture. In other cases, it is convenient and preferred to carry out the reaction in the additional presence of an inert solvent to allow the reaction to proceed at a suitable rate of reaction. Preferred inert solvents are aprotic in nature and include hydrocarbons and halogenated hydrocarbons (e.g. benzene, toluene, chloroform, chlorinated benzenes and the like). Aliphatic and alicylic ethers may also be used.

The reaction may be readily carried out by placing all of the reaction mixture components in a reaction vessel having agitation and heating means. The reaction may also be carried out under an inert atmosphere (e.g. nitrogen). The mode of addition of reactants, base and solvent is not critical to the present invention.

The reaction temperature is preferably from about 0° C. to about 100° C.; more preferably from about 40' C. to about 70° C. It is also preferred to employ atmospheric pressure; but lower or higher than atmospheric pressure may also be used.

The reaction time should normally be long enough to result in optimum reaction yield. The exact optimum time will depend upon many other reaction parameters such as reaction temperature and particular solvent employed. Generally, reaction times from about 5 to about 10 hours are suitable and longer reaction times are not needed.

In accordance with the present invention, the adducts derived from formulae (I) and (II), above, may be utilized as effective stabilizers of organic materials against oxidative degradation. In practicing the process of the present invention, an effective stabilizing amount of one or more of these compounds is added to an organic material normally subject to oxidation degradation such as polyolefins (e.g. plastics and the like) or functional fluids (e.g. hydrocarbon distillate fuels, hydrocarbon lubricant oils and greases and non-hydrocarbon or synthetic oil base stocks, distillate fuels, lubricant oils and greases) or fats or natural oils. It is to be understood that the term "effective stabilizing amount against oxidative degradation" as used in the specification and claims herein is intended to include any amount that will prevent or control the oxidative degradation of said organic material. The term "oxidative degradation" as used herein includes both non-catalyzed oxidation and transition metal-catalyzed (e.g. copper-catalyzed oxidation) caused by thermal or long-term aging effects or the like. Of course, this stabilizing amount may be constantly changing because of the possible variations of many parameters. Some of these parameters include the specific organic material to be protected; the specific compound of the present invention used as an antioxidant; the geometry and environment of the organic material to be protected; temperature; and the like.

The antioxidant compounds of this invention may be preferably used in concentrations ranging from about 0.001% to about 10% by weight of the organic material. More preferably, this concentration may range from about 0.005% to about 5% by weight of the organic material.

Polyolefins in which the compounds of this invention may be added include α-olefin polymers, such as polyethylene (including crosslinked), polypropylene, polyisobutylene, polybutene-1, polymethylbutene-1, polymethylpentene-1, polyisoprene and polybutadiene. Also included are copolymers of the monomers of which the above homopolymers are based, such as ethylenepropylene copolymers, propylene-butylene-1 copolymers, ethylene-butylene-1 copolymers, ethylene-hexene-1 copolymers, propylene-isobutylene copolymers, styrene-butadiene copolymers, and terpolymers of ethylene and propylene with a diene (e.g. hexadiene, dicyclopentadiene or ethylidenenorbornene). Also included are mixtures of the above-mentioned homopolymers, such as a mixture of polypropylene and polyethylene, polypropylene and polybutene-1, or polypropylene and polyisobutylene. Polypropylene and polyethylene, as well as copolymers and polymer mixtures containing propylene and ethylene units, are preferred.

The incorporation of the compounds of the present invention into organic material may be effected by any conventionally known method for adding antioxidants to organic materials. In the case of polyolefins as the substrate, it may be advantageous to add or mix the compounds of the present invention either before, during or after the polymerization reaction. If done after the polymerization, they may be mixed into the polymer melt either before or during shaping or by applying a dispersion of these compounds to the surface of shaped polymeric article.

Various known inhibitors and additives may also be added with the antioxidant compounds of this invention to the organic composition such as functional fluids. These other additives and inhibitors further control or modify various chemical and physical properties of polyolefins. The general term "inhibitor" is used for those additives which increase resistance to chemical changes.

Included among the various types of other additives which may be added to polyolefins of this invention are: other antioxidants, antiozonants, thermal stabilizers, ultraviolet light absorbers, coloring materials, dyes, pigments, other metal chelating agents, and the like.

Included among the various types of other additives which may be added to the functional fluids of this invention are: inhibitors for pH and corrosion control, other antioxidants, rust inhibitors, viscosity-index improvers, pour-point depressants, wear additives, lubricating additives, antifoaming agents, metal deactivators, metal passivators, stabilizers, deemulsifiers, dyes, and odor supressants.

Generally, the total amount of other additives which may be incorporated into the organic composition will vary depending on the particular composition and the desired properties. More particularly, the total amount of other additives will comprise from 0 to 20 percent and preferably from 0.1 to 8.0 percent by weight based on the total weight of the organic composition.

The following Examples further illustrate the present invention. All parts and percentages are by weight unless otherwise explicitly stated.

EXAMPLE 1

Preparation of Methyl 2,3,4,6-Tetra-O-[2-(3,5-di-tert-butyl-4-hydroxyphenol)propanoyl]-α-D-glucopyranoside A mixture of 0.58 g (0.003 moles) methyl α-D-glucoside and 4.36 g (0.015 moles) 2-(3,5-di-tert-butyl-4-hydroxyphenyl)propanoyl chloride in 50 ml dry pyridine was heated at 65°–70 C. for 20 hours under a nitrogen atmosphere. The resulting orange-yellow reaction mixture was then cooled to room temperature and poured into 100 ml ice water. After decanting the cloudy aqueous portion, a yellow-brown oil remained. This oil was further worked up by first being dissolved in 50 ml chloroform. This chloroform solution was washed with aqueous sodium bicarbonate (5% NaHCO$_3$ by weight) (1×100 ml) and water (1×100 ml) and dried over MgSO$_4$. Flash evaporation gave a yellow viscous oil which was dried in vacuo over P$_2$O$_5$ to give 3.46 g (93% yield) of an off-white solid product, mp 72°–75° C. This above-titled compound by IR and NMR analysis and by elemental analysis:

Anal. Calc. for C$_{75}$H$_{110}$O$_{14}$: C, 72.90; H, 8.97.
Found: C, 72.88; H, 9.06.

EXAMPLE 2

Preparation of Methyl 2,3,4,6-Tetra-O-(3,5-di-tert-butyl-4-hydroxybenzoyl)-α-D-glucopyranoside A mixture of 0.97 g (0.005 moles) methyl α-D-glucoside and 7.10 g (0.025 moles) 3,5-di-tert-butyl-4hydroxybenzoyl chloride in 50 ml dry pyridine was stirred and heated under a nitrogen atmosphere at 65°–70° C. for 21 hours. After a work-up in the same manner as that described in Example 1, 0.75 g (14% yield) of a light yellow solid, mp 163°–166° C., was isolated. This product was identified as the above-titled compound by IR and NMR analysis and by elemental analysis: Anal. Calc. for C$_{67}$H$_{94}$O$_{14}$: C, 71.63; H, 8.43.
Found: C, 71.65; H, 8.33.

EXAMPLE 3

Preparation of 2,3,4,6-Tetra-O-[2-(3,5-di-tert-butyl-4-hydroxyphenyl)-propanoyl]-D-glucopyranose A mixture of 0.90 g (0.005 moles) D-glucose and 7.27 g (0.025 moles) 2-(3,5-di-tert-butyl-4hydroxyphenyl)-propanoyl in chloride 50 ml dry pyridine was stirred and heated at 60°–70° C. for 21 hours nitrogen atmosphere. After a work up in the same manner as Example 1, 1.10 g (10% yield) of an off-white solid, mp 86°–94° C. dec, was isolated. This product was identified as the above-titled compound by IR and NMR analysis and by elemental analysis:

Anal. Calc. for C$_{74}$H$_{108}$O$_{14}$: C, 72.75; H, 8.91.
Found: C, 72.07; H, 8.05.

EXAMPLE 4

Preparation of 2,3,4,6-Tetra-O-(3,5-di-tert-butyl-4-hydroxybenzoyl)-D-glucopyranose A mixture of 0.90 g (0.005 moles) and 7.10 g (0.025 moles) 3,5-di-tert-butyl-4-hydroxybenzoyl chloride in 50 ml dry pyridine was stirred under nitrogen at 51°–53° C. for 48 hours. After a work up in the same manner as Example 1, 1.70 g (19% yield) of an off-white solid, mp 173°–178° C., was isolated. This product was identified as the above-titled compound by IR and NMR analysis and by elemental analysis:

Anal. Calc. for C$_{66}$H$_{92}$O$_{14}$: C, 71.45; H, 8.36.
Found: C, 71.38; H, 7.84.

EXAMPLE 5

Preparation of 1,3,4,5Tetra-0-[2-(3,5-di-tert-butyl-4hydroxyphenyl)-propanoyl]-D-fructofuranose A mixture of 0.90 g (0.005 moles) D-fructose and 7.27 g (0.025 moles) 2-(3,5-di-tert-butyl-4-hydroxyphenyl)propanoyl chloride in 50 ml dry pyridine was stirred and heated under a nitrogen atmosphere at 60°–70° C. for 20 hours. After a work up in the same manner as in Example 1, 6.95 g (quantitative yield) of an off-white solid was isolated. This product was identified as the above-titled compound by IR and NMR analysis and by elemental analysis:

Anal. Calc. for C$_{74}$H$_{108}$O$_{14}$: C, 72.75; H, 8.91
Found: C, 72.81; H, 8.78.

EXAMPLE 6

Preparation of 1,3,4,5-Tetra-0-(3,5-di-tert-butyl-4-hydroxybenzoyl)-D-fructofuranose A mixture of 0.90 g (0.005 moles) D-fructose and 7.10 g (0.025 moles) 3,5-di-tert-butyl4-hydroxybenzoyl chloride in 50 ml dry pyridine was stirred and heated at 51°–53° C. for 48 hours under nitrogen. After a work up in the same manner as Example 1, 0.55 g (10% yield) of an off-white solid, mp 169°–171° C. dec, was isolated. This product was identified as the above-titled compound by IR and NMR analysis and by elemental analysis:

Anal. Calc. for C$_{66}$H$_{92}$O$_{14}$: C, 71.45; H, 8.36.
Found: C, 71.84; H, 8.20.

INDUCTION PERIOD SCREENING FOR 40% CYCLOHEXENE/60% HEPTANE

The procedures of ASTM D525 as modified for automatic data acquisition were followed to measure the effect of the compounds of Examples 1 and 3–6 on the induction period of the test fluid (40% cyclohexene/60% heptane). The screening protocol involved measuring the induction period increase (IPI) in minutes of the test fluid containing 10 mg/L of additive over a standard test fluid containing no additive.

The screening results for these compounds is outlined in TABLE I. The induction period increase is the increase in the amount of time before the onset of oxidative degradation relative to the onset of oxidation degradation in the unstabilized fluid. The numbers are recorded in minutes. Therefore, the induction period increase is equal to (Induction period of fluid +test additive) - (Induction period of fluid).

TABLE I

| Example | Induction Period Increase (IPI) |
|---|---|
| 1 | 199 |
| 3 | 150 |
| 4 | 31.2 |
| 5 | 119 |
| 6 | 16.9 |
| WYTOX 540 @ | 29.6 |

@WYTOX 540 is a polymeric phenol phosphite antioxidant/stabilizer commercially available from Olin Corporation of Stamford, Connecticut.

SCREENING IN POLYOLEFINS

Several antioxidants, including the compounds of Examples 1 and 5, above, were incorporated into two standard test resins (i.e. polypropylene and linear low density polyethylene) along with any processing aids by (5 room temperature twin-shell blending of all ingredients for a sufficient period of time (4-24 hours) to yield a homogeneous mixture.

The blended homogeneous mixtures were then separately extruded through a Brabender single screw extruder set at an appropriate temperature profile (i.e. 200°-260° C. for both polypropylene and linear low density polyethylene). An adjustable ribbon die was used to extrude sheets of varying thickness (5-50 mil films) and a rod die was used for extrusion with subsequent pelletization with a Brabender Pelletizer. The extruded sheets and pellets were used for oven aging and melt index screening, respectively.

A. Screening In Polypropylene

All antioxidant candidates were extruded in Hercules 6501 polypropylene resin at a concentration of 0.2%. The adjustable ribbon die was set to produce a 25 mil sheet. Samples (~3×4 inches) were cut from the sheet and oven aged at 150° C. in a forced air oven. Hunter color readings were measured on the initial sheet and on the sheet at failure. Yellowness index data and hours to failure for these antioxidant compounds are outlined in TABLE II. The yellowness index was measured with a Hunter color apparatus. The higher the number, the more yellow the polymer is, which of course is undesired. In the case of no additive, good color is observed. Therefore, the color test does not measure polymer degradation. Failure is defined as the hours required in the hot air oven for loss of polymer properties (e.g. plasticity). The higher the number, the longer the time the antioxidant stabilizes the polypropylene against degradation.

As can be seen in TABLE II, the antioxidant of Examples 1 and 5 compared favorably against standard commercially available antioxidants in both the color and time to failure tests.

TABLE II

| Compound | Yellowness Index Initial | Yellowness Index Failure | Hours to Failure |
|---|---|---|---|
| Polypropylene alone | 0.49 | (b) | 24 |
| Example 1 | 1.88 | 21.02 | 334 |
| Example 5 | 10.91 | (b) | 70 |
| WYTOX PAP (c) | 7.18 | 28.09 | 47 |
| IRGANOX 1076 (d) | 0.81 | 12.24 | 116 |
| CYANOX 1790 (e) | 5.14 | 37.09 | 116 |

(b) Yellowness index could not be read at failure due to the brittleness of the sample.
(c) WYTOX PAP is a polymeric hindered phenol antioxidant commercially available from Olin Corporation of Stamford, Connecticut.
(d) IRGANOX 1076 is a medium molecular weight hindered phenol antioxidant commercially available from Ciba-Geigy Corporation of Hawthorne, New York.
(e) CYANOX 1790 is a high molecular weight hindered phenol antioxidant commercially available from American Cyanamid Company of Stamford, Connecticut.

B. Screening In Polyethylene

All antioxidant candidates were extruded in Exxon linear low density polyethylene resin (LLDPE) (melt index 0.760/density 0.918) at a concentration of 0.05%. Two extrusion dies were used (i.e. a ribbon die adjusted to give 25 mil sheets and a rod die which was used in conjunction with a Brabender pelletizer).

The sheets were extruded using two formulations for each candidate. The first formulation incorporated the candidate additive alone, and the second formulation incorporated the candidate additive with 0.05% by weight WYTOX 312 and 0.75% by weight calcium stearate. The films were aged in a forced air oven at 60° C. for 30 days. Hunter color readings were read on the initial sheets and also after 15 and 30 days of oven aging. The results are outlined in TABLE III. WYTOX 312 is tris nonylphenyl phosphite antioxidant synergist made by Olin Corporation of Stamford, Conn. and used to help control color problems with hindered phenols. Calcium stearate is a lubricant for processing. The data shown in TABLE III indicates that the antioxidants of Examples 1 and 5 are less discoloring over a period of time as compared to standard commercially available antioxidants.

In the rod die extrusion followed by the pelletization test, the formulation incorporated the candidate additive alone. Melt Indexes (MI) were measured during multiple extrusions for these samples. The results are outlined in TABLE IV. The Melt Index is a measure of polymer degradation. Generally with polyethylene a lower Melt Index means more polymer degradation via crosslinking. Accordingly, high MI values are desired. As seen in TABLE IV, the products of Examples 1 and 5 compare favorably with the known standards.

TABLE III

| Compound | Formulation (f) | Yellowness Index Initial | 15 days | 30 days |
|---|---|---|---|---|
| Exxon LLDPE alone | A | −0.85 | 0.52 | 0.38 |
|  | B | −1.09 | 0.08 | −0.06 |
| Example 1 | A | 3.20 | 5.01 | 5.84 |
|  | B | 2.40 | 9.70 | 6.83 |
| Example 5 | A | 7.69 | 10.32 | 10.76 |
|  | B | 6.48 | 12.25 | 13.60 |
| CYANOX 1790 | A | 8.83 | 13.77 | 14.51 |
|  | B | 3.55 | 8.58 | 11.07 |
| IRGANOX 1076 | A | 0.74 | 3.59 | 5.05 |
|  | B | −0.30 | 2.98 | 5.48 |

(f) Formulation A = 0.05% candidate additive
Formulation B = 0.05% candidate additive plus 0.05% WYTOX 312 plus 0.075% calcium stearate.

TABLE IV

| Compound | Melt Index First Extrusion | Second Extrusion | Third Extrusion |
|---|---|---|---|
| Exxon LLDPE alone | 0.533 | 0.493 | 0.459 |
| Example 1 | 0.629 | 0.613 | 0.605 |
| Example 5 | 0.642 | 0.638 | 0.641 |
| CYANOX 1790 | 0.657 | 0.614 | 0.604 |
| IRGANOX 1076 | 0.669 | 0.637 | 0.649 |

What is claimed is:

1. An oxidation-inhibited composition comprising an organic material normally subject to oxidative degradation containing an effective stabilizing amount against oxidative degradation of a 4-acyl-2,6-dialkylphenol adduct of a saccharide derived from either formula (I) or (II):

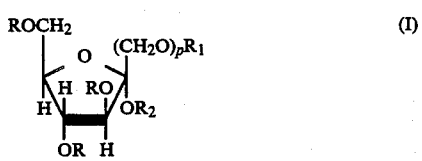

-continued

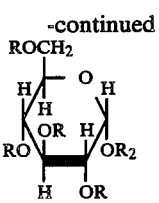
(II)

wherein p is defined as being 0 or 1; R is defined as a hydrogen or 4-acyl-2,6-dialkylphenol of formula (III):

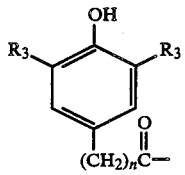
(III)

with the proviso that at least one of said R in formula (I) or (II) is said 4-acyl-2,6-dialkylphenol; $R_1$ is defined as a hydrogen when p =0 and as a R when p=1; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

2. The oxidation-inhibited composition of claim 1 wherein each $R_3$ is a tert-butyl group and n is from 2 to 6.

3. The oxidation-inhibited composition of claim 2 wherein $R_2$ is hydrogen or methyl.

4. The oxidation-inhibited composition of claim 3 wherein each R is said 4-acyl-2,6-dialkylphenol of formula III.

5. The oxidation-inhibited composition of claim 1 wherein said organic material is polyolefin.

6. The oxidation-inhibited composition of claim 5 wherein said polyolefin is an α-olefin polymer.

7. The oxidation-inhibited composition of claim 6 wherein said α-olefin polymer is selected from polypropylene and polyethylene.

8. The oxidation-inhibited composition of claim 1 wherein said effective stabilizing amount against oxidative degradation is from about 0.001% to about 10% by weight of said organic material.

9. A process for stabilizing an organic material normally subject to oxidative degradation which comprises adding to said organic material an effective stabilizing amount against oxidative degradation of a 4-acyl-2,6-dialkylphenol adduct of a saccharide derived from either formula (I) or (II):

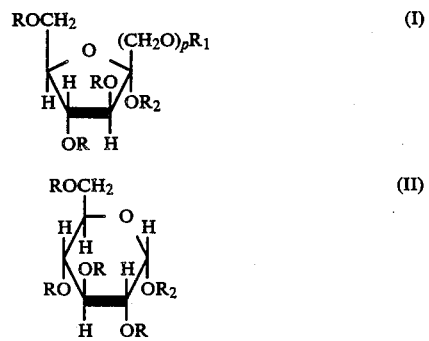

wherein p is defined as being 0 or 1; R is defined as a hydrogen or 4-acyl-2,6-dialkylphenol of formula (III):

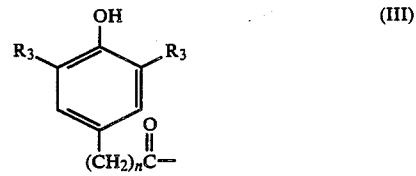
(III)

with the proviso that at least one of said R in formula (I) or (II) is said 4-acyl-2,6-dialkylphenol; $R_1$ is defined as hydrogen when p =0 and as a R when p =1; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

10. The process of claim 9 wherein each $R_3$ is a tert-butyl group and n is from 2 to 6.

11. The process of claim 10 wherein $R_2$ is hydrogen or methyl.

12. The process of claim 11 wherein each R is said 4-acyl-2,6-dialkylphenol of formula III.

13. The process of claim 9 wherein said organic material is polyolefin.

14. The process of claim 13 wherein said polyolefin is an α-olefin polymer.

15. The process of claim 14 wherein said α-olefin polymer is selected from polypropylene and polyethylene.

16. The process of claim 9 wherein said effective stabilizing amount against oxidative degradation is from about 0.001% to about 10% by weight of said organic material.

17. A 4-acyl-2,6-dialkylphenol adduct of a saccharide derived from either formula (I) or (II):

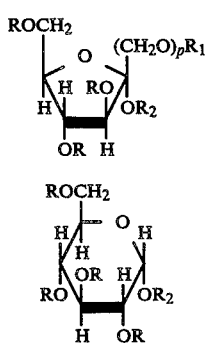

wherein p is defined as being 0 or 1; R is defined as a hydrogen or 4-acyl-2,6-dialkylphenol of formula (III):

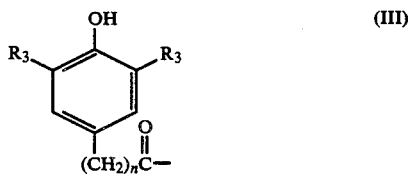
(III)

with the proviso that at least one of said R in formula (I) or (II) is said 4-acyl-2,6-dialkylphenol; $R_1$ is defined as hydrogen when p =0 and as a R when p =1; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

18. The compound of claim 17 wherein each $R_3$ is a tert-butyl group.

19. The compound of claim 18 wherein n is from about 2 to about 6.

20. The compound of claim 19 wherein n is 2.

21. The compound of claim 20 wherein each R is said 4-acyl-2,6-dialkylphenol radical.

22. A compound of the formula selected from the group consisting of:

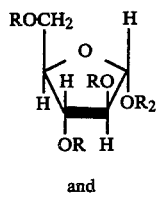
(I)

and

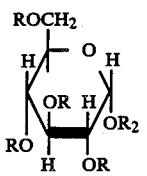
(II)

where R is defined as a 4-acyl-2,6-dialkylphenol of formula (III):

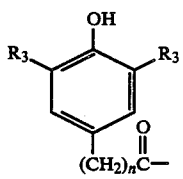
(III)

$R_2$ is a lower alkyl group having 1 to 4 carbon atoms; each $R_3$ is selected from the group consisting of branched alkyl groups having from about 4 to about 8 carbon atoms; and n is defined as being from 0–10.

23. A compound for formula (IA):

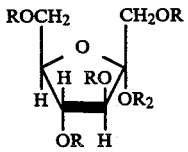
(IA)

wherein R is defined as a hydrogen or a 4-acyl-2,6-dialkylphenol of formula (III):

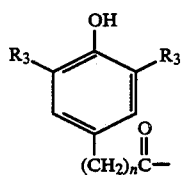
(III)

with the proviso that at least one of said R in formula (IA) is said 4-acyl-2,6-dialkylphenol; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

24. A compound of either formula (I) and (II):

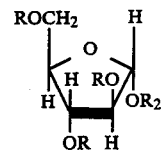
(I)

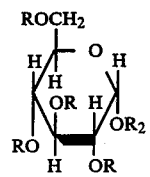
(II)

wherein R is defined as a hydrogen or 4-acyl-2,6,-dialkylphenol of formula (III):

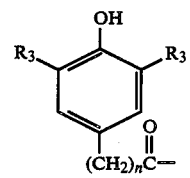
(III)

with the proviso that at least one of said R in formula (I) or (II), but not all, is said 4-acyl-2,6-dialkylphenol group; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

25. A compound of the formula selected from the group consisting of:

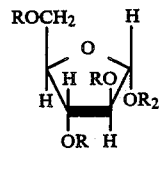
(I)

and

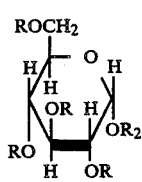
(II)

where R is defined as 4-acyl-2,6-dialkylphenol of formula (III):

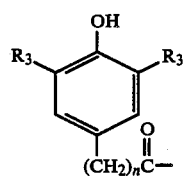
(III)

$R_2$ is a hydrogen; each $R_3$ is selected from the group consisting of branched alkyl groups having from about 4 to about 8 carbon atoms; and n is defined as being from 0–10.

26. An oxidation-inhibited organic material comprising an organic material normally subject to oxidative degradation containing an effective stabilizing amount against oxidative degradation of a compound of the formula selected from the group consisting of:

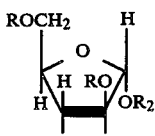
(I)

and

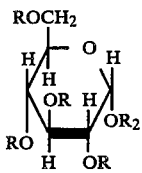
(II)

where R is defined as a 4-acyl-2,6-dialkylphenol of formula (III):

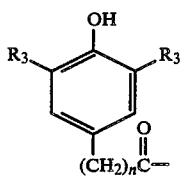
(III)

$R_2$ is a lower alkyl group having 1 to 4 carbon atoms; each $R_3$ is selected from the group consisting of branched alkyl groups having from about 4 to about 8 carbon atoms; and n is defined as being from 0–10.

27. An oxidation-inhibited organic material comprising an organic material normally subject to oxidative degradation containing an effective stabilizing amount against oxidative degradation of a compound of formula (IA):

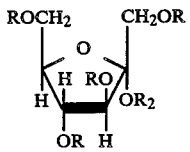
(IA)

wherein R is defined as a hydrogen or a 4-acyl-2,6-dialkylphenol of formula (III):

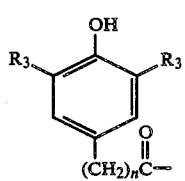
(III)

with the proviso that at least one of said R in formula (IA) is said 4-acyl-2,6-dialkylphenol; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

28. An oxidation-inhibited organic material comprising an organic material normally subject to oxidative degradation containing an effective stabilizing amount against oxidative degradation of a compound of either formula (I) and (II):

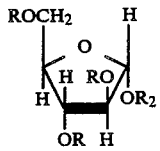
(I)

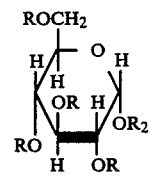
(II)

wherein R is defined as a hydrogen or 4-acyl-2,6-dialkylphenol of formula (III):

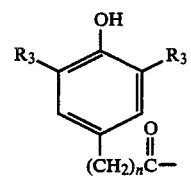
(III)

with the proviso that at least one of said R in formula (I) or (II), but not all, is said 4-acyl-2,6-dialkylphenol group; $R_2$ is selected from the group consisting of hydrogen and a lower alkyl group having 1 to 4 carbon atoms; each $R_3$ is selected from the group consisting of branched alkyl groups having about 4 to about 8 carbon atoms; and n is defined as being from 0 to 10.

29. An oxidation-inhibited organic material comprising an organic material normally subject to oxidative degradation containing an effective stabilizing amount against oxidative degradation of a compound of the formula selected from the group consisting of:

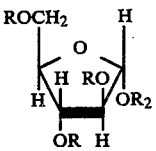
(I)

and

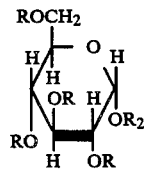
(II)

where R is defined as a 4-acyl-2,6-dialkylphenol of formula (III):

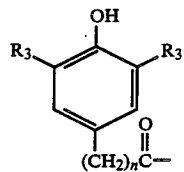
(III)
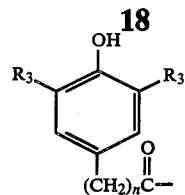
(III)
$R_2$ is a hydrogen; each $R_3$ is selected from the group consisting of branched alkyl groups having from about 4 to about 8 carbon atoms; and n is defined as being from 0-10.
* * * * *
$R_2$ is a hydrogen; each $R_3$ is selected from the group consisting of branched alkyl groups having from about 4 to about 8 carbon atoms; and n is defined as being from 0-10.
* * * * *